United States Patent [19]
Tan et al.

[11] Patent Number: 5,804,744
[45] Date of Patent: Sep. 8, 1998

[54] APPARATUS FOR OBTAINING, STORING AND TRANSPORTING LIQUID SAMPLES AND METHODS FOR MAKING AND USING SAME

[75] Inventors: Samantha S. H. Tan, Fremont; Dianne M. Dougherty, Menlo Park, both of Calif.

[73] Assignee: Chemtrace, Hayward, Calif.

[21] Appl. No.: 723,861

[22] Filed: Sep. 30, 1996

[51] Int. Cl.⁶ .................................................. G01N 1/00
[52] U.S. Cl. ......................................................... 73/864.34
[58] Field of Search .................................. 215/316, 329, 215/DIG. 4; 220/288, 86.1, DIG. 14; 73/864.14, 864.31, 864.34, 864.35, 864.51, 864.62, 864.63, 864.91; 128/767, 768

[56] References Cited

U.S. PATENT DOCUMENTS

| | | |
|---|---|---|
| 3,603,156 | 9/1971 | Konkol . |
| 3,718,133 | 2/1973 | Perry et al. . |
| 3,796,542 | 3/1974 | Kline .................................... 128/767 |
| 3,809,068 | 5/1974 | Kosowsky . |
| 3,951,313 | 4/1976 | Coniglione . |
| 4,118,195 | 10/1978 | Beach .................................. 73/864.62 |
| 5,507,194 | 4/1996 | Scavuzzo et al. ................... 73/864.63 |
| 5,622,183 | 4/1997 | Hazard et al. ......................... 128/767 |

FOREIGN PATENT DOCUMENTS 1 031 641  6/1966  United Kingdom ................... 128/767

*Primary Examiner*—Robert Raevis
*Attorney, Agent, or Firm*—Hickman & Martine, LLP

[57] ABSTRACT

A low contamination bottle for sampling, storing, and transporting of chemical samples includes a bottle portion defining an internal volume and having a threaded neck, and a cap portion provided with threads that engage the threaded neck of the bottle to provide a fluid-tight seal between the internal volume of the bottle and the ambient environment. The bottle has a flexible sidewall portion that permits the reduction of the internal volume to allow a liquid sample to be drawn into the bottle portion by a suction or vacuum process. Both the bottle portion and the cap portion are made from a material selected from the chemical resistant group consisting essentially of hydrocarbon polymers and fluorocarbon polymers, where the material generates less then 1 ppb of metal contaminants and 1 ppm of leachable anionic and organic contaminants. The flexible sidewall portion of the bottle portion has a minimum thickness of 0.2 mm such that the low contamination bottle meets all safety requirements for the transport of hazardous chemical samples.

20 Claims, 10 Drawing Sheets

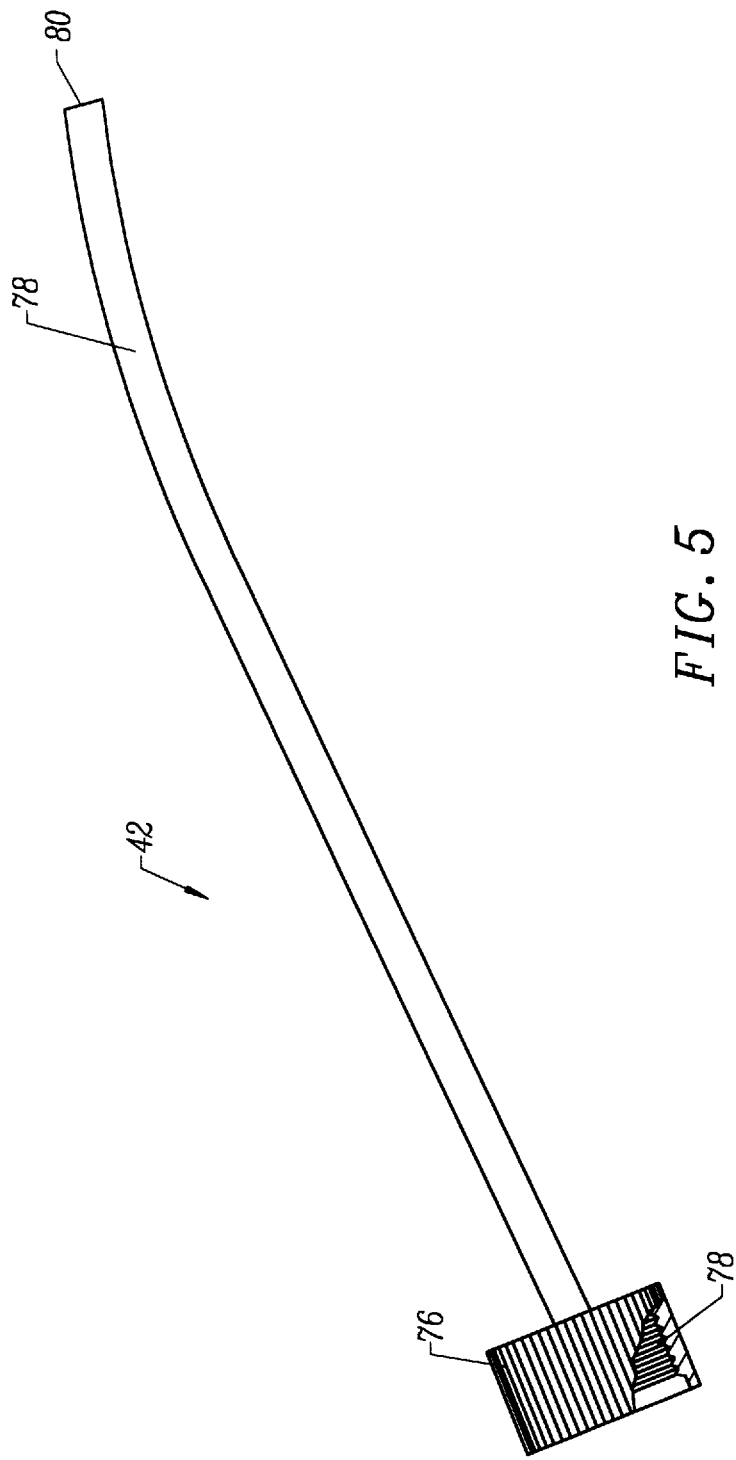

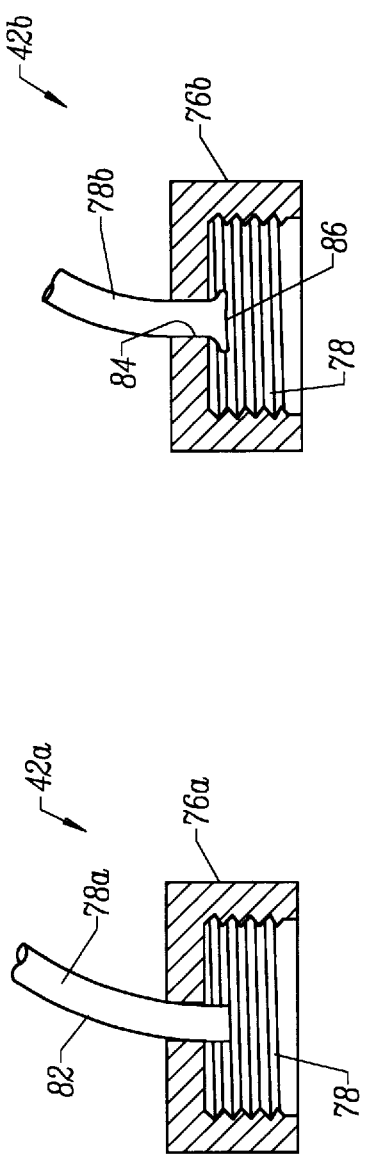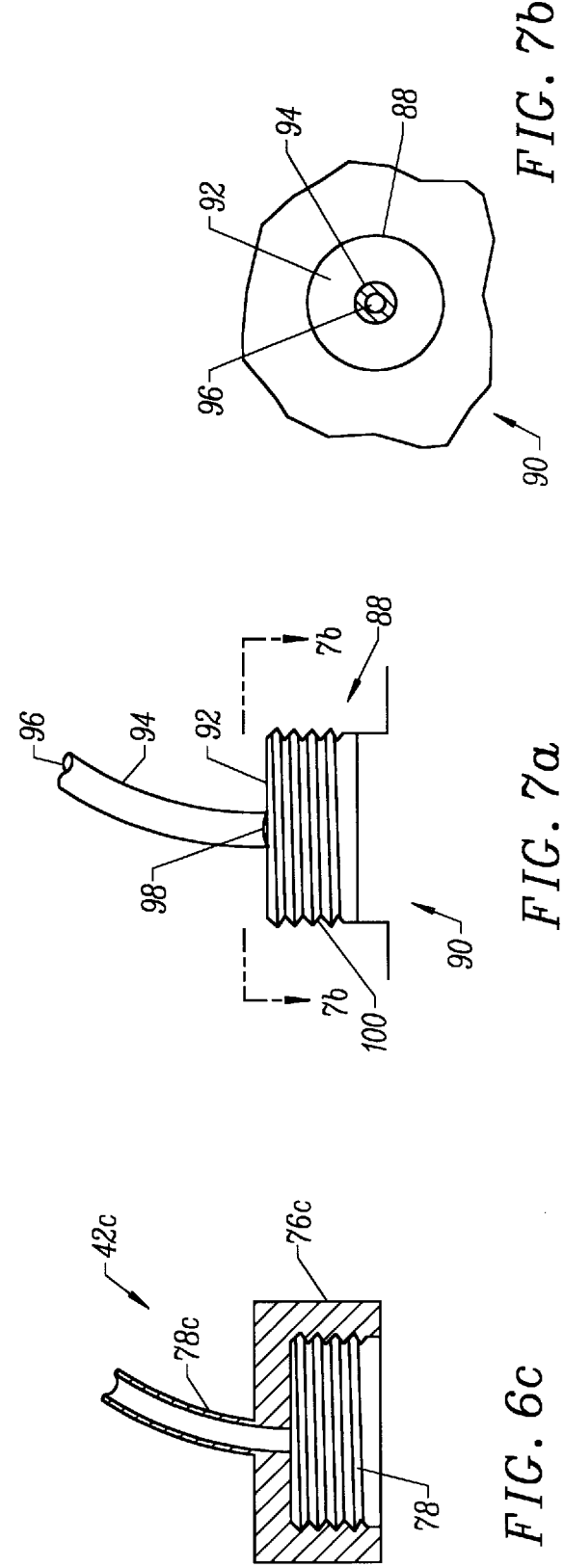

APPARATUS FOR OBTAINING, STORING AND TRANSPORTING LIQUID SAMPLES AND METHODS FOR MAKING AND USING SAME

DESCRIPTION

1. Technical Field

This invention relates to devices and methods for sampling high purity liquid substances for the purpose of chemical analysis. More specifically, the present invention relates to methods and apparatus for obtaining, storing, and transporting chemical samples without the introduction of contaminants into the samples, as well as to methods for manufacturing sampling devices.

2. Background Art

The chemical analysis of liquid samples is required for a number of industries. For example, ground water may be sampled for toxic impurities, crude oil may be tested for sulfur content, and wine may be sampled to test its sugar content. In all cases, a mechanism is provided to extract a sample from the body of the liquid, and a container is provided to hold and/or transport the sample to a testing station. For certain types of chemical testing, it is important that the extraction mechanism and he container do not introduce contaminants that could affect the test results concerning the liquid sample.

In the semiconductor manufacturing industry, the problem of obtaining a non-contaminated liquid sample is critical. A large number of liquid chemicals are used to process semiconductor wafers to create integrated circuits thereon. As the line widths of integrated circuits shrink to the sub-micron range, the purity of the liquid chemicals used in the processing becomes more and more critical. Compared to other industries, the maximum tolerable level of impurities in the process chemicals are at least a factor of 100 to 1000 times lower. Depending upon the type of contaminant, maximum contaminant levels in semiconductor processing chemicals can be specified in the low parts-per-million (ppm), parts-per-billion (ppb), and even parts-per-trillion (ppt) range. Contaminants in the processing liquids in excess of the specified levels can be damaging to the semiconductor manufacturing process, thereby decreasing integrated circuit "yield" and increasing costs.

Semiconductor processing facilities are typically referred to as "fabs." A fab includes a "clean room" environment wherein airborne particulates are held to a minimum. Within the clean room are a variety of semiconductor manufacturing "tools", i.e. specialized equipment that perform manufacturing processes on semiconductor wafers. Some of these tools are "wet tools" which utilize liquid chemicals such as etchants, photoresist, developers, strippers, etc.

Most modern fabs obtain their processing chemicals in bulk, e.g. in 55 gallon drums. These chemicals include concentrated caustic, poisonous and corrosive chemicals such as hydrofluoric acid, hydrochloric acid, sulfuric acid, phosphoric acid, ammonium hydroxide, etc. These chemicals are then distributed to the various semiconductor processing tools through a Bulk Chemical Distribution System (BCDS) to various tools, holding tanks, and baths, etc. within the fab. For example, the BCDS can distribute wafer cleaning fluids to a "wet station" or "bath" where wafers are cleaned. Alternatively, the BCDS can pump processing fluids to a temporary "day tank" (i.e. a storage tank in which the process chemical are continuously recirculated through filters to reduce particles), or it can pump processing fluids directly to a "point of use", such as to a semiconductor tool.

As noted above, the various liquid chemicals used in processing semiconductors must be very pure, e.g. trace metal contaminants must be kept to ppb and sub-ppb levels. The contaminants with which process engineers are most concerned are typically metal particles, although anionic and organic contaminants are becoming of more concern of late.

The semiconductor manufacturing industry has identified at least thirty-five metal contaminants that can degrade the semiconductor manufacturing process. In particular, nine metal contaminants are of great concern in the semiconductor manufacturing industry at levels of greater than 0.1–1.0 ppb. These metals are aluminum (Al), iron (Fe), chromium (Cr), nickel (Ni), sodium (Na), calcium (Ca), potassium (K), copper (Cu), and Zinc (Zn). These metals are particularly damaging to the semiconductor manufacturing process since they are common impurities in cleaning chemicals used in the manufacturing process and in the tool components themselves, and also tend to show up on the wafer during processing.

The highest purity chemicals available to industry are made for semiconductor manufacturing purposes. These very expensive semiconductor-grade chemicals guarantee metallic impurities at less than 1.0 ppb (Ashland Chemicals "megabit" grade), or less than 0.1 ppb (Ashland Chemicals "gigabit" grade). Obviously, the liquid chemicals being used must also be pure at the point of use, e.g. at a semiconductor manufacturing tool, at the wet station, etc. This requires that the liquid chemicals are not only pure at the bulk storage container (e.g. at the 55 gallon drum or at the day tank), but they also must not acquire undesirable impurities as they are being distributed by the BCDS.

To avoid yield loss and downtime during device manufacturing, process chemicals needs to be monitored for all types of impurities (especially metals) on a routine basis. Most fabs maintain very comprehensive Quality Control (QC) monitoring programs to test the purity of their chemicals as purchased, and at various points through the distribution system. This requires clean sampling devices and techniques. Sampling without contamination is a very important issue since the chemicals are of very high purity. For critical cases, sampling apparatus and procedures must not contribute more than 50–100 ppt of impurities.

There are some apparatus and devices available to sample process chemicals. However, none of these apparatus or devices are ideal. They tend to be somewhat cumbersome and expensive, and often contribute unacceptable levels of impurities into the chemical samples.

For example, there are currently some very expensive liquid sampling panels that can be built into equipment that handle the process liquids or into the BCDS which distributes the process liquids. However, despite the sophistication of the semiconductor manufacturing industry, there is currently no convenient, economical, and effective way to take a very clean chemical sample from a drum, a day tank, or an open bath at a wet station.

Finding a sampling device that is clean enough for the application and is also compatible with the corrosive and concentrated chemicals used in the semiconductor industry is a problem in the prior art. For example, some fab technicians use glass pipettes or glass syringes for obtaining samples from bulk containers of liquid. However, glass pipettes and syringes tend to contaminate the samples with sodium and boron, and are totally unsuitable for some common chemicals such as hydrofluoric acid (HF). When using the glass pipette or glass syringe method to obtain, for example, a sample of a strong acid, up to 200 ppb of boron can be introduced into the sample.

Plastic sampling devices such as plastic pipettes and plastic syringes introduce their own forms of contaminants, typically including hundreds of ppb of contaminants such as Ca, Zn, Na, K, and Fe. Furthermore, the O-rings that provide sliding seals within syringes leach sodium, iron, and zinc into the liquid. Obviously, if the fab engineers are concerned with contamination at the low ppb or in the ppt range, such high levels of contamination are unacceptable.

Fab technicians have used lengths of Teflon tubing to obtain liquid samples by inserting a first end of the tubing into the bulk container, placing their thumb over the free end of the tubing, and withdrawing the tubing from the container with the liquid sample. This technique can introduce a substantial amounts of human contamination (Na, K, etc.) into the sample, and also can be quite dangerous for the technician working with these often caustic and poisonous materials. Still other fab technicians use ladles to scoop a sample from the bulk container, which is not only a health hazard but also can contaminate the liquid in the bulk container as well as the obtained sample.

Other types of sampling devices include rigid spouts with pumping mechanisms, pressure differential systems, bailer systems, etc. However, all of these sampling apparatus suffer from one or more of the following drawbacks:
1) they are made from chemically incompatible material such as polypropylene;
2) the materials that they are made from are not clean enough;
3) they can not be used in a clean enough manner;
4) they are too complex or too expensive to use in routine manner; and
5) they are unsafe for use with certain chemicals.

For example, at one major wafer fab, a heated vacuum system was designed to force sample fluid into a sample bottle through a system of pre-cleaned tubes, valves and pumps. With all of its technical merit, the system took so long to set up and operate that it wasn't used during a recent set of experiments on bath lifetime and, instead, a much simpler sampling apparatus was used. This simpler sampling apparatus was used even though the device selected could only be used once, was not very compatible with chemicals (it was made from polypropylene), and needed extensive pre-cleaning prior to use.

There has been some attempt in the commercial market to address the problem of obtaining samples of from open vessels. However, the vast majority of companies that create liquid sampling devices are interested mass market applications (e.g. environmental testing) where testing methodologies can tolerate much higher levels of impurities. For example, sampling devices for ground water analysis are plentiful. However, sampling for the semiconductor manufacturing industry is quite specialized, and requires relatively few and small volumes of high purity liquid samples to be obtained compared, for example, to the environmental industry. Therefore, the commercial market has not placed a great detail of emphasis on developing sampling devices for the semiconductor manufacturing business.

One sampling device that has been specifically designed for obtaining clean samples from drums and other bulk containers for the semiconductor manufacturing industry and is disclosed in U.S. Pat. No. 4,930,360 of Tan, an inventor of the present invention. While the disclosed "liquid sampler" is a great improvement over pipettes, lengths of PFA tubing, and ladles, it does have a number of drawbacks. For one, the liquid sampler of Tan requires a vigorous pumping action to create a vacuum to draw the liquid from the container. In addition to the mechanical difficulty of the vigorous pumping action, particulates are formed by surface-to-surface friction between the moving parts of the device. For example, the O-rings used to maintain the seal between a piston a cylinder of the device can fall into and contaminate the liquid sample. In addition, the often corrosive materials sampled by the device can attack the various seals and valves of the device, causing the degradation of the device and possibly further contaminating of the liquid being collected. Finally, the liquid sampler disclosed by Tan is a relatively complex and, once contaminated, a hard-to-clean device, making reuse of the device difficult.

As noted above, the prior art does not provide a good method or apparatus for obtaining a clean sample from a container such as a drum chemical, bath, or day tank. In addition, prior art containers for storing and/or transporting the liquid samples have also had their problems. Typically, the samples are stored and/or shipped in pre-cleaned Teflon bottles manufactured by such companies as Nalgene (distributed by VWR in the U.S.), Norton Performance Plastics Corporation (Wayne, N.J.), and the Japanese company Korubo.

Teflon (made from IIFA or FEP resin materials) is currently considered to be the cleanest material available and is used extensively throughout the semiconductor industry for low contamination applications. However, even with a Teflon product, the pre-cleaning required to assure that all impurities have been leached from the contaminant surfaces is laborious and expensive. Typically, a pre-cleaned Teflon bottle is sequentially soaked in two types of concentrated acids for upwards of 2 weeks and then rinsed for 7 days in ultra-pure water.

As can be expected, such Teflon bottles can be quite expensive. As a result, they tend to be cleaned and reused. However, even the cleaning process can be quite expensive, e.g. $10–$20 per bottle. Therefore, a lower cost or even disposable bottle for holding and transporting samples would be desirable.

Some sampling bottles are made by a process known as "blow molding." One type of such prior art sampling bottles is a sampling bottle made from polypropylene resin that is provided with a snap-on cap. Such a prior art bottle is suitable for certain non-hazardous liquids such as water, but is not useful or safe for storing or transporting samples of most chemicals used in semiconductor manufacturing processes. Certain other manufacturers of these bottles have produced bottles suitable for holding and transporting clean chemicals out of polyethylene (PE) materials. Such bottles, while relatively free of impurities, are too large and are of an unsuitable configuration for sampling fluids. For example, PurePak Technology of Arizona has produces a low particulate, low metallic content, one gallon size bottle. This gallon jug can be used to store high purity chemicals without the need for pre-cleaning due to a "clean manufacturing process" adopted by the manufacturer. The clean manufacturing process involves obtaining clean polyethylene resin, manufacturing in a clean room environment, filtering the gas to the blow molding machine, and pre-cleaning the blow molding machine prior to a production run of bottles.

It should be noted that polypropylene bottles are not appropriate for the collection or transport of hazardous liquids in that are incompatible with many corrosive liquids, and often (to not have a leak-proof threaded cap as required under the U.S. Department of Transportation (DOT) regulations. Therefore, there is no interest in the semiconductor manufacturing industry in using inexpensive polypropylene bottles, even if they are pre-cleaned, for holding and shipping chemical samples. Further, there is little interest in using polypropylene samplers, such as the polypropylene bellows pump available from Acron Industries (Livonia, Mich.), for the obtainment of liquid samples in the semiconductor industry for similar reasons.

It should be noted that the current method of sampling liquids uses a first device to obtain a sample, a second device to contain the sample, and possibly a third device in which to ship the sample. This requires multiple transfers of the liquid sample and multiple opportunities for contamination due to those transfers. It is therefore desirable to minimize the number of transfers of a liquid sample between its removal from the bulk liquid until it is reaches the analytical laboratory where it is to be tested.

DISCLOSURE OF THE INVENTION

The present invention solves the long-felt need for an inexpensive, easy to use, and effective method for obtaining clean chemical samples for subsequent chemical analysis. More particularly, the present invention provides a method and apparatus for obtaining liquid chemical samples without introducing trace contaminants such as metals, anions, and organics at the parts per billion (ppb) levels.

A method for manufacturing a low contamination sampling device for the sampling, storage, and transport of chemical samples begins with the provision of a clean manufacturing environment (such as a clean room). The method further provides within the clean manufacturing environment, a very clean, low metallic resin selected from the group consisting of essentially of chemically resistant hydrocarbon polymers (e.g. polyethylene or "PE") and fluorocarbon polymers (e.g. perfluoroalkoxy or "PFA", fluorinated ethylene propylene or "FEP", and polyetheretherketone or "PEEK"). Most preferably, the low metallic resin contains less than 1 ppb of leachable metal contaminants and 1 ppm of leachable anionic and organic contaminants.

Also provided within the clean manufacturing environment is a blow molding machine. A source of low contamination gas is coupled to the blow molding machine. The blot molding machine is "prepared" (i.e. cleaned) prior to a manufacturing run, or a dedicated blow molding machine is used. A bottle is blow molded within the blow molding machine using the low contamination ("clean") resin and low contamination ("clean") gas. Next, a solid, threaded cap made from a resin material selected from the group consisting essentially of chemical resistant hydrocarbon polymers and fluorocarbon polymers as described above, where again the resin contains less than 1 ppb of leachable metal contaminants and 1 ppm of leachable anionic and organic contaminants.

The cap is immediately affixed to a threaded neck of the bottle as it comes of the mold within the clean manufacturing environment to produce a fluid-tight seal between the cap and the bottle. By producing the low contamination sampling bottle by the aforementioned method, it is not generally necessary to pre-clean or pre-condition the bottle prior to obtaining a chemical sample. By capping the bottle immediately after production while the bottle is hot and positively pressurized from the cooling action, few contaminants are able to come into contact with the internal surfaces of the bottle. Any human handling of the bottle during its manufacture is accomplished with appropriate clean manufacturing techniques, e.g. at least with the use of clean room gloves and preferably with cap, gown and face mask.

While a low contamination sampling bottle of the present invention can be produced by several methods, the polyethylene form of the product is preferably produced by the process. The low contamination bottle manufactured thereby includes a bottle portion having a threaded neck, and a cap portion provided with threads that engage with the threaded neck of the bottle portion to provide a leak proof seal. The bottle portion defines an internal volume, and has flexible sidewalls which permit the reduction of the internal volume of the bottle portion in response to an applied pressure (e.g by squeezing). The bottle portion is made from a material selected from the group consisting essentially of chemical resistant hydrocarbon polymers and fluorocarbon polymers as set forth above, where the material contains less than 1 ppb of leachable metal contaminants and 1 ppm of leachable anionic and organic contaminants. The flexible sidewall portion has a minimum thickness of 0.2 millimeters (mm).

A low contamination sampling kit for obtaining chemical samples includes a bottle having a flexible sidewall which permits the reduction of the internal volume in response to an applied pressure. The bottle is provided with a threaded neck. A sampling head including a threaded cap engageable with the threaded neck of the bottle, and a tube communicating with the internal volume of the bottle. The sampling head is preferably made from the same types of materials used in making the bottle.

A method for sampling, storing, and transporting chemical samples includes:

(a) providing a sealable bottle including a bottle portion and a sampling head portion, the bottle portion defining an internal volume, the bottle portion having a flexible sidewall portion which permits the reduction of the internal volume in response to an applied pressure, the bottle portion having a threaded neck, the cap portion being provided with threads that are engaged with the threaded neck to provide a fluid-tight seal, the bottle and sampling head being made from a material selected from a group consisting essentially of chemical resistant hydrocarbon polymers and fluorocarbon polymers, where the flexible sidewall portion of the bottle portion have a minimum thickness of 0.2 mm;

(b) exerting a force on the flexible sidewall portion to reduce the internal volume of the bottle portion;

(c) inserting a first end of the tube of the sampling head into a liquid chemical to be sampled, other end of the tube communicating with the internal volume of the bottle portion, where the tube is made from a material selected from the group consisting essentially of chemical resistant hydrocarbon polymers and fluorocarbon polymers;

(d) removing the force from the flexible sidewall portion of the bottle portion to allow the internal volume of the bottle portion to increase, thereby drawing a liquid chemical to be sampled through the tube and into the bottle portion; and (e) re-sealing the bottle with a solid cap for the storage and/or transport of the chemical sample without transferring the chemical made from sample to another container.

The present invention is advantageous in that it is a low cost, easy-to-use, low contamination method and apparatus for sampling, storing, and shipping a high purity chemical sample. In many instances, the specialized manufacturing process eliminates the need for pre-c leaning the bottle. Furthermore, since the same bottle is used for pulling, storing, and transporting a sample, only one bottle or container (instead of two or three) would need to be cleaned if cleaning were deemed necessary for very critical applications.

Unlike some prior art methods, contaminants are not introduced into the chemical sample by contacting the sample with non-chemically inert or unclean surfaces. Neither is the present invention particularly expensive compared to prior art sampling devices. Further, the apparatus of the present invention is safe, easy to use and easy to manufacture compared to apparatus of the prior art that serve a similar function but may not be compatible with certain chemicals used in the semiconductor manufacturing industry.

These and other advantages of the present invention will become apparent upon reading the following detailed descriptions and studying the various figures of the drawings.

BRIEF DESCRIPTION OF THE DRAWINGS

FIG. 5 is a partially broken side view of a sampling head of the present invention;

FIG. 6a–6c are cross sectional views illustrating several preferred embodiments for the sampling head of FIG. 5;

FIGS. 7a and 7b illustrate an alternate embodiment for the bottle portion with built-in sampling tube of the present invention;

BEST MODES FOR CARRYING OUT THE INVENTION

Figure 1:
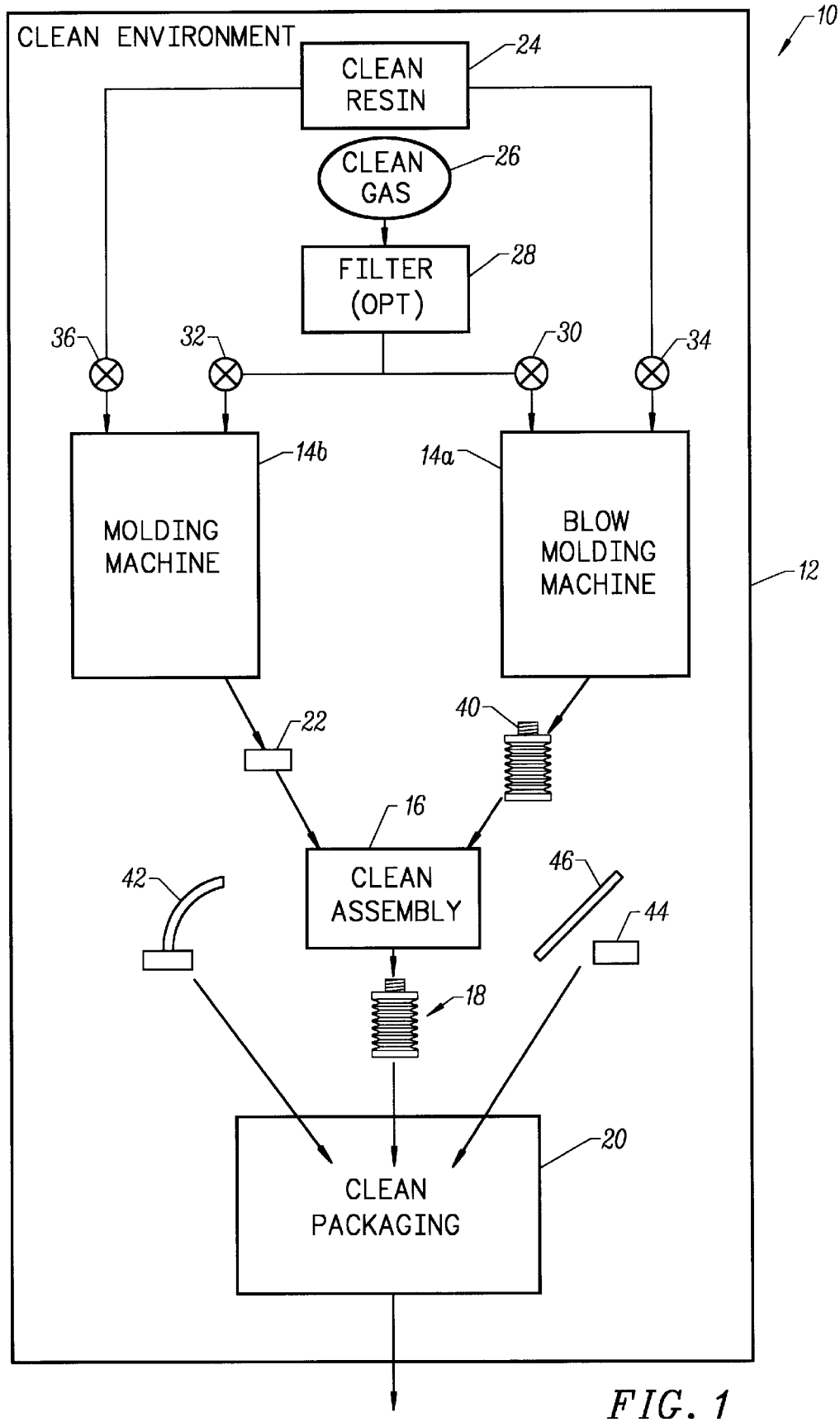
In FIG. 1, a block-diagram illustrating a method and manufacturing system for producing low-contamination sampling device for sampling, storing, and transporting chemical samples.

In FIG. 1, a system 10 for manufacturing a low contamination sampling bottle includes a clean environment 12, one or more molding machines 14 and 14b, and a clean assembly station 16. The system 10 is designed to produce a low contamination sampling bottle 18, which can be optionally packaged with other items in a clean packaging or "sampling kit" 20. Preferably, the manufacture of the bottle 18 takes place entirely within the clean environment 12 such that the bottle 18 does not need to be pre-cleaned or pre-conditioned prior to use.

The construction of a clean environment 12 (sometimes referred to as a "clean manufacturing room" or "clean room") is well-known to those skilled in the art. Typically, clean rooms are sealed from the ambient environment and air filtration systems are used to filter particulates from the air within the clean room. Clean rooms come in various grades, such as a class 1000 clean room, a class 100 clean room, a class 10 clean room, etc., where the lower the number, the cleaner the room. The actual cleanliness of the room for manufacturing purposes in this invention varies with the desired cleanliness of the product. The machinery or "tools" within the clean room are often automated to minimize the contamination introduced by human operators. Human operators are typically gloved and gowned, and may be masked or "bunny suited" to reduce the human contamination factor.

As part of the process for manufacturing a low contamination sampling bottle, a solid threaded cap, such as threaded cap 22, is provided within the clean environment 12. By "solid" it is meant herein that when the cap is engaged with a bottle portion, the cap can provide a fluid-tight (i.e. a gas and liquid tight) seal with the bottle portion, which is leak proof. The cap 22 can be produced within the clean environment 12, such as by a molding machine 14b, or it can be produced outside of the clean environment 12 and then introduced into the clean area 12 as a previously manufactured product. If the cap 22 is produced within the clean environment 12, it will have a contamination of less than 1 ppb of leachable metal and less than 1 ppm of leachable anions and organics without the need for a cleaning step (referred to herein as a "clean cap"). If the cap 22 is produced outside of clean room 12, it will likely require a pre-cleaning to reduce its contamination to the aforementioned level. Methods for cleaning objects, such as cap 22, to remove metallic and ionic contaminants are well-known to those skilled in the art. Such cleaning may include a nitrogen purge step.

The method for manufacturing a low contamination sampling bottle of the present invention further includes providing within the clean environment 12, a supply of low contamination (low metallic and anionic and organic contamination) resin 24 that is preferably of chemically resistant hydrocarbon polymers (e.g. polyethylene or "PE") and fluorocarbon polymers (e.g. perfluoroalkoxy or "PFA", fluorinated ethylene propylene or "FEP", and polyetheretherketone or "PEEK"). FEP, PFA and PTFE are sold under the trademark Teflon® by DuPont de Nemours, Inc., (Wilmington, Del.). To be suitable for use with the present invention, the resin should contain less than 1 ppb of leachable metal contaminants and 1 ppm of leachable anionic and organic contaminants after being molded into a product (referred to herein as "clean resin").

The process also includes providing within the clean environment 12 at least one blow molding machine, e.g. blow molding machine 14. A source of clean gas 26 is coupled to the blow molding machine 14 by a valve 30. An optional filter 28 may be provided to further filter residual particulates from the clean gas 26. As used herein, "clean gas" has a similar meaning as when that term is used in the semiconductor manufacturing industry. In the present embodiment, the source of gas 26 is also coupled to a second or "cap" molding machine 14b by a valve 32. The molding machine 14b can be any suitable type of molding machine for the manufacture of the cap, e.g an injection molding machine. Similarly, clean resin 24 is coupled to blow molding machine 14 by a valve 34 and to cap molding machine 14b by a valve 36.

The blow molding machine 14 is prepared for each "manufacturing cycle" or "production run" of sampling bottle portions 38. More particularly, filters are changed and the surfaces of the blow molding machine 14 that come in contact with the resin 24 may be cleaned to remove contaminants. Similarly, if the cap 22 is produced within the clean room 12, the molding machine 14b is cleaned prior to a production run of caps 22. Either of these methodologies provide a "clean blow molding machine", as referred to herein.

Once the blow molding machine 14 has been prepared and is ready to go, a number of sampling bottle portions 38 are produced by the blow molding machine 14 using the clean resin 24 and the clean gas 26. Methods for operating commercially available blot molding machines are well-known to those skilled in the art. Typically, the clean gas 26 is either HEPA filtered air or pure nitrogen ($N_2$). As the bottle portions 38 are produced, a gloved, masked, and hair netted (or even "bunny suited") operator assembles the cap 22 onto the threaded neck 40 of the bottle portion 38 to produce the assemble bottle 18 in a clean assembly area 16. The assembled bottle 18 can be inserted into a sampling kit 20 along with an assembled sampling head 42, or with an unassembled sampling head in the form of a sampling head cap 44 and a separate tube 46. Preferably, the sampling kit 20 includes a low-contamination polyethylene bag (one type of "clean packaging") which can be sealed to protect the kit components from contamination prior to use.

Figure 2:
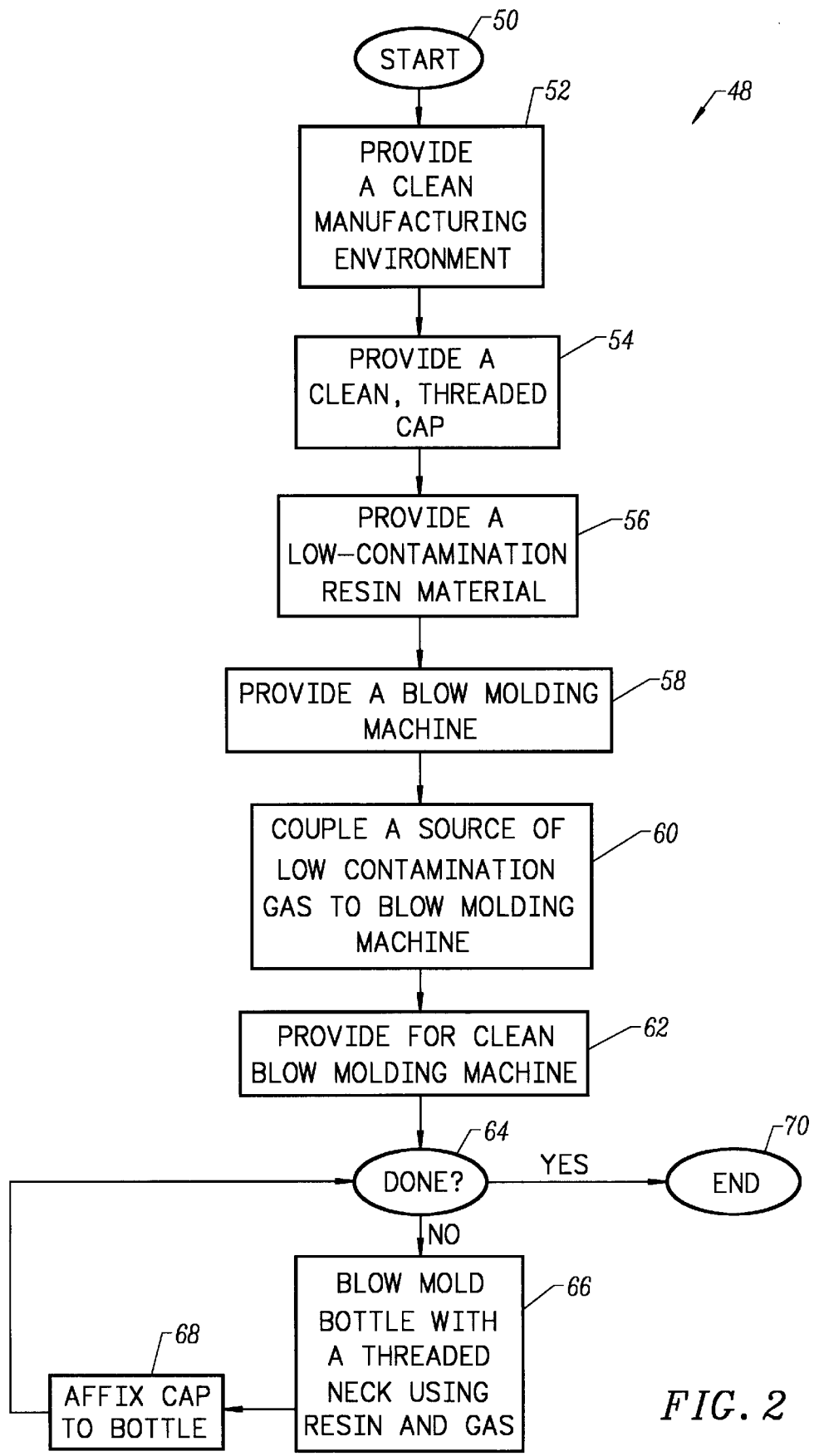
FIG. 2 is a flow-diagram of the process of the present invention for producing the low contamination bottle.

In FIG. 2, a process 48 for manufacturing a low-contamination sampling bottle in accordance with the present invention begins at 50 and, in a step 52, a clean manufacturing environment is provided. Next, in a step 54, a clean PFA, polytetrafluoroethylene ("PTFE"), or PE cap is provided within the clean room manufacturing environment. In a step 56, a low-contamination resin is provided, and in a step 58, a blow molding machine is provided in the clean manufacturing environment. Step 60 couples a source of clean gas to the blow molding machine, and a clean blow molding machine is provided in step 62. Step 62 is accomplished by thoroughly cleaning the blow molding machine, or by dedicating the blow molding machine to only the production of the clean bottle portions.

In step 64, it is determined whether the process 48 is completed and, if not, a step 66 blow molds a bottle portion having a threaded neck using the clean resin and the clean gas. The threaded cap is affixed to the threaded neck of the bottle in a step 68 and process control returns to step 64. Of course, multiple sampling bottle portions can be manufactured prior to the threading of cap onto the neck of a particular bottle portion. When step 64 determines that the manufacturing process of "production run" is completed, the process terminates as indicated at 70.

It should be noted that the bottle portions 38 can be manufactured and stored within the clean environment for some time before the caps are screwed onto their necks. However, it is considered to be desirable to attach the caps to the bottle portions as soon as possible after the manufacture of the bottle to reduce the chance for contaminating the insides of the bottle portion.

In addition, it is considered desirable to attach the caps to the bottle portions while the bottle portions are still heated ("warm") from the blow molding process. This is because warm air anti/or other warm gasses within the bottle portions create a slight positive pressure within the bottle portions, reducing the chance that airborne contaminants from the surrounding environment might enter the bottle portion. Therefore, capping the bottle while it is still warm reduces the level of cleanliness required for the "clean environment", e.g. an environment that is less clean than a standard "clean room" can be used.

It should also be noted that the manufacture of fluorocarbon sampling bottles and caps is considerably different from the manufacture of hydrocarbon (e.g. polyethylene) bottles and caps. The manufacture of fluorocarbon based materials requires the blow molds to be resistant to fluorine gas that is generated during the blow molding process. This gas needs to be exhausted since it is harmful to operators. The fluorine gas also causes corrosion of the blow molds and additional maintenance of the blow mold is required. However, the solutions to these special problems of blow molding fluorocarbon articles of manufacture are well known to those skilled in the art. Even though fluorocarbon type materials (e.g. Teflon®) formed into bottles are inherently cleaner than hydrocarbon materials (e.g. polyethylene) formed into bottles, the added difficulty and expense of the manufacturing process for fluorocarbons may make that process less desirable than the manufacturing process for hydrocarbons.

Figure 3:
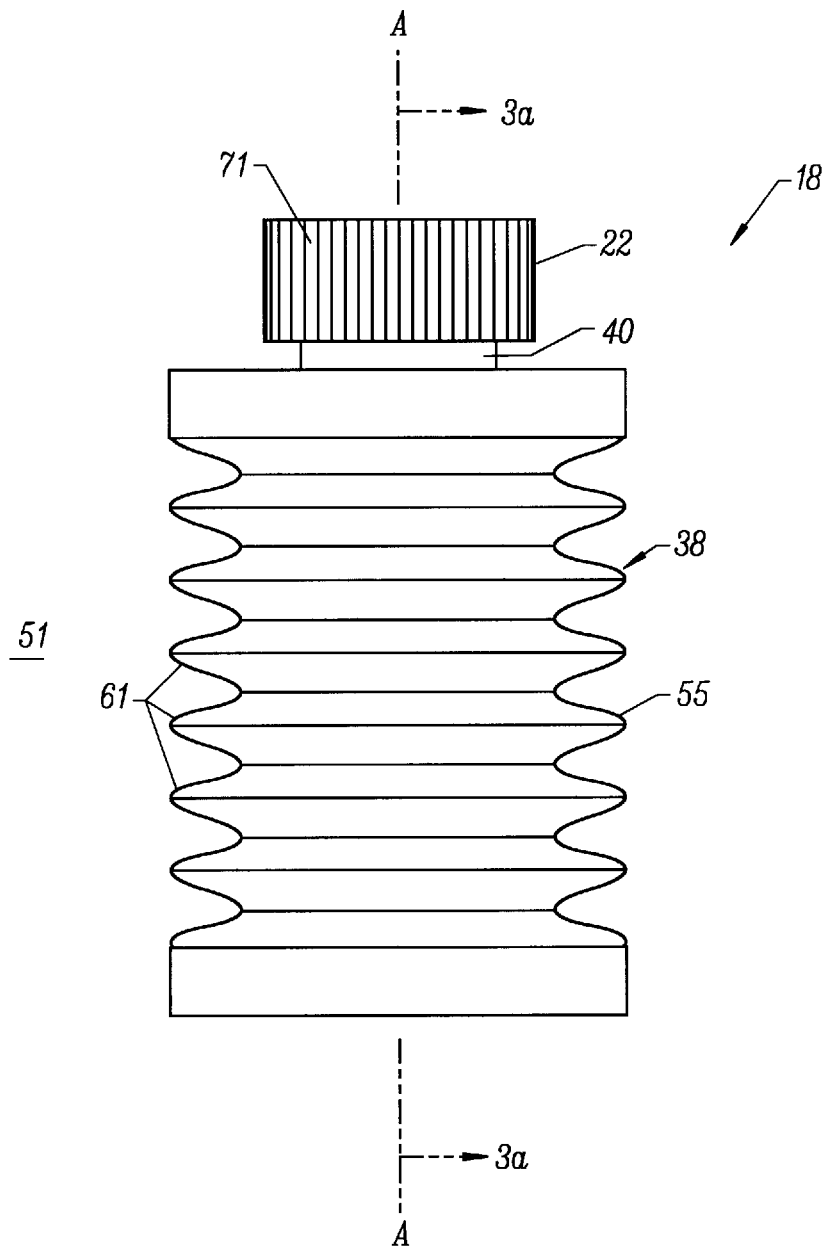
FIG. 3 is a low contamination sampling bottle of the present invention.

In FIG. 3, an assembled sampling bottle 18 includes the bottle portion 38 and the solid cap 22. The threaded cap 22 is engaged with the threaded neck 40 of bottle portion 38 such that a fluid-tight seal is formed, preventing contamination of the interior of the bottle portion 38 with the ambient environment 51, and preventing liquids within the bottle 18 from leaking past the cap. With additional reference to the cross sectional view of FIG. 3a, the bottle portion 38 defines an internal volume 53 and includes a flexible sidewall section 55 that permits the internal volume 53 to be reduced. More particularly, if a force F is applied to the bottle portion 38, such as between a base surface 57 and shoulder surface 59, the bottle portion 38 will partially collapse such that the base surface 57 is at 57' and the shoulder surface 59 is at 59'. This greatly reduces the internal volume 53 of the bottle portion 38. As will be discussed in detail subsequently, the release of the force F will allow the bottle portion 38 to expand to its uncompressed condition, creating a suction or vacuum force to draw liquid chemical samples into the internal volume 53 of the bottle portion 38.

In a preferred embodiment of the present invention, the interior volume of the bottle 18 (when undeformed) is between about 30 milliliters (ml) and about 1000 ml, more particularly between about 30 ml and about 500 ml, and still more particularly between about 30 ml and 250 ml. In one particular embodiment, the internal volume is about 125 ml.

Figure 3A:
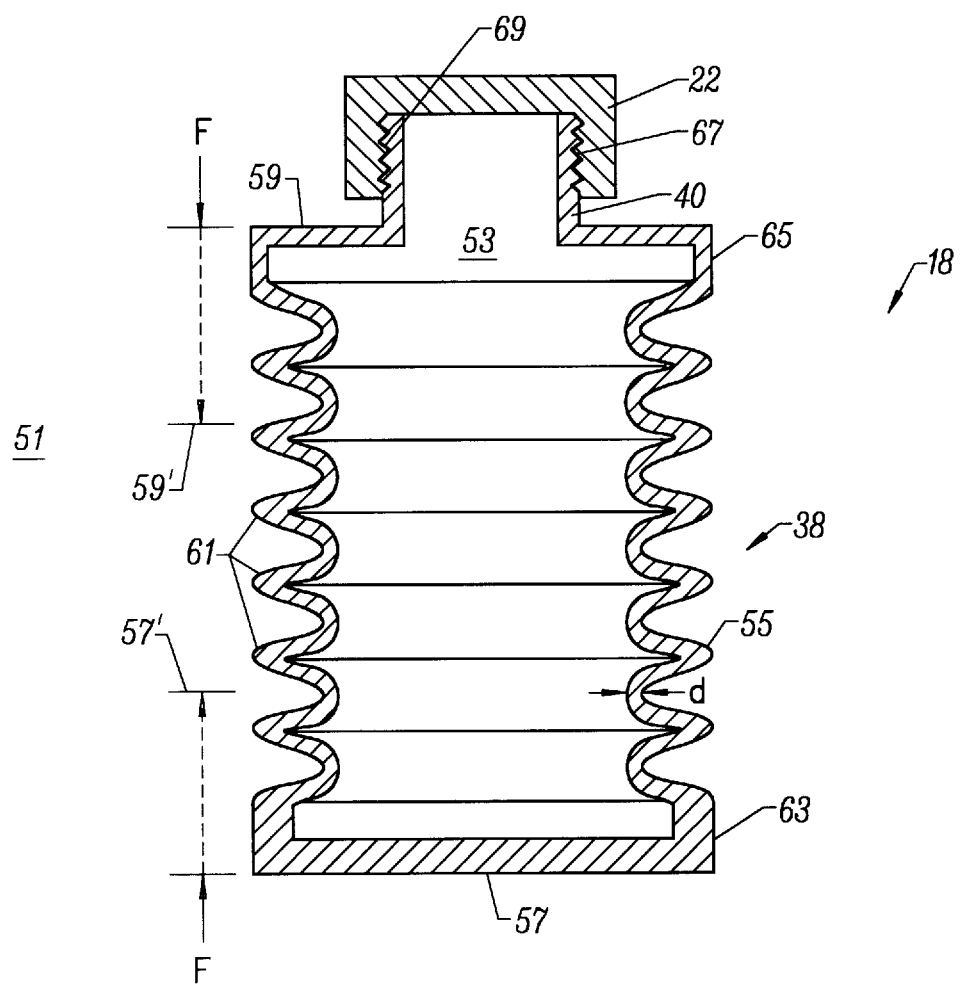
FIG. 3a is a cross sectional view taken along line 3a—3a of FIG. 3.

In the embodiments of FIGS. 3 and 3a, the flexible sidewall section includes a number of "accordion folds", "bellow folds", or "pleats" 61 which permits the bottle to be partially collapsed as previously described. In this preferred embodiment, the pleats are formed concentrically around a vertical axis A of the bottle portion 38 to allow a vertical compression of the bottle portion. The bottle portion 38 also includes a base portion 63 including the base surface 57, and a shoulder portion 65 including the shoulder surface 59. The neck 40 includes a threaded section 67 which engages complimentary threads 69 provided on an inner diameter of the cap 22. The cap 22 may be provided with knurls 71 or other texturing to provide a better finger grip.

As used herein, the cap 22 will be described as a "solid" cap in that when the cap 22 is engaged with the threaded neck 40 of bottle portion 38, the internal volume 53 is isolated from the ambient environment 51. As will be noted subsequently during the discussion of an alternate embodiment for the cap 22, the cap 22 including a sampling tube is also "solid" if the sampling tube is capped or sealed.

Both the bottle portion 38 and the cap portion 22 are preferably made from a material selected from the group consisting essentially of chemical resistant hydrocarbon polymers e.g. polyethylene (PE) and fluorocarbon polymers such as PFA, FEP, PTFE, and PEEK. However, it should be noted that the bottle portion 38 and cap 22 do not have to made out of the same material. For example, body 38 can be made from polyethylene, while the cap 22 can be made from PFA or FEP. As another example, bottle portion 38 can be made from high density polyethylene, while the cap 22 can be made from a low density polyethylene.

It should be noted that there are both low density polyethylene and high density polyethylene resins available on the market. Low density polyethylene is easier to work with and is more flexible (ie. more "plastic"), but is less chemically resistant than high density polyethylene. The present invention contemplates the use of a "medium density" polyethylene by mixing low density polyethylene resin with high density polyethylene resin to produce a blend that is easier to work with and more flexible than high density polyethylene, but which is more chemically resistant than low density polyethylene.

The described materials are preferred because they can be manufactured in a clean fashion, are chemically inert to the chemicals of interest, and are compatible with the chemicals of interest. Since all three of these features are important, the terms "clean", "chemically inert", and "chemically compatible" will be described below.

Of the two preferred material types of the present invention, polyethylene is desirable in at it is relatively inexpensive and is easier to work with than fluorocarbon polymers. When manufactured into a bottle portion and/or cap of the present invention, the resultant article of manufacture includes less than 1 part per billion (ppb) of leachable metallic contaminants and less than 1 part per million (ppm) of leachable anionic and organic contaminants, both on the surface of the article and being "leachable" from the materials of the article of manufacture by the sampled liquid.

Fluorocarbon polymers are relatively more expensive and are harder to work with, but have the advantage of being commonly accepted in the semiconductor industry for high purity applications. The process of the present invention produces a fluorocarbon bottle and cap which also has leachable metallic contaminants of less than 1 ppb, and leachable anionic and organic contaminants less than 1 ppm.

By "clean," it is meant that the material, whether it be polyethylene or a fluorocarbon, will not introduce contaminants into a liquid sample in excess of the aforementioned contaminant levels. Again; these contaminants can be present on the surface of the material that is in contact with the liquid, or can be "leached" from the material of the bottle or cap by thy liquid. By "chemically inert" it is meant tat the chemical samples will not substantially change the chemical or physical properties the bottle material. By "compatible" it is meant that the chemical samples are physically compatible with characteristics of the material such as the material's porosity. In other words, a chemical sample can be considered to be incompatible with the material (even if it is chemically inert with respect to that material) if the sample, due to small molecular size and high mobility, has the ability to migrate through microscopic pores in the walls of the bottle.

The aforementioned materials have been found to be chemically inert and compatible with most chemicals used in the manufacture of semiconductors. For example, the materials of the bottle and cap of the present invention are both chemically inert and compatible with hydrofluoric acid (HF), hydrochloric acid (HCL), sulfuric acid ($H_2SO_4$), phosphoric acid ($H_3PO_4$), nitric acid ($HNO_3$), hydrogen peroxide ($H_2O_2$), ammonium hydroxide ($NH_4OH$), tetramethyl ammonium hydroxide (TMAH), and isopropyl alcohol (IPA). However, the material of the polyethylene embodiment of the present invention is not fully compatible and chemically inert to most developers, strippers and photoresists used in semiconductor manufacturing processes. Fluorocarbon embodiments of the present invention are chemically inert and compatible with all of the mentioned chemicals.

Figure 4:
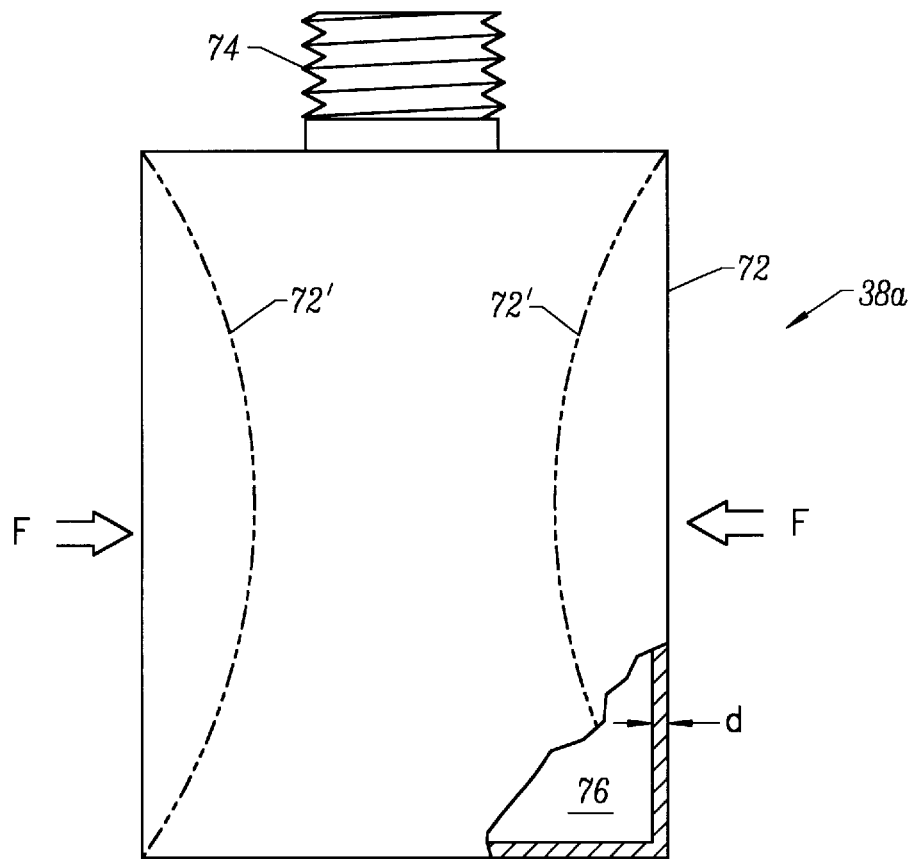
FIG. 4 is an alternate embodiment for the bottle portion of the low contamination sampling bottle of the present invention.

In FIG. 4, an alternate embodiment for a bottle portion 38a includes a generally cylindrical sidewall 72 and a threaded neck 74. The sidewall 72 can be "squeezed" by a force F to obtain a new position 72', which reduces the internal volume 76 of the bottle portion 38a. The bottle portion 38a is less difficult to design and manufacture than the previously describe "pleated" type bottle, but may not permit the same level of reduction of internal volume 76 as the previously described embodiment. Also, the pleated design may be more suitable for use with high density polyethylene, since the design will permit even this stiffer material to flex sufficiently to deform the sidewalls of the bottle portion. With the embodiment of FIG. 4, a medium density or low density polyethylene is preferred to promote sidewall flexibility.

It should be noted that are many equivalent bottle designs to the bottle designs shown in FIGS. 3/3a and 4. For example, a bottle can be made with vertical pleats, rather than horizontal pleats. The essential characteristics of the bottle portion of the present invention is that it will have wall portions that can be deformed in some fashion to reduce the internal volume of the bottle portion such that a liquid can be drawn into the internal volume upon the release of the force. The bottle portions of the p)resent invention also do not include any seals, O-rings or friction surfaces which can degrade and/or introduce contaminants into the liquid sample.

The bottle of the present invention serves three very important functions. First, the bottle can be used to obtain a sample of a liquid from, for example, a drum, bath, or other open body of liquid. Secondly, the same bottle can be used to store the chemical sample for extended periods of time, e.g. to satisfy the need of certain manufacturers retained "archive" samples from each lot of material as part of their quality assurance program due to its chemical inertness and compatibility with the liquids. Finally, the same bottle can be used to transport the chemical sample to, for example, an analytical laboratory for analysis.

The function of obtaining a liquid sample will be discussed in greater detail subsequently. The storage of the chemical sample (such as for archival purposes) is made possible due to the low contamination methodology of the present invention, and to the long-term chemical inertness and compatibility of the aforementioned materials with the chemicals in question. The issue of the shipment ("transport") of a chemical sample in the bottle of the present invention includes some subtleties, which will be discussed below.

Chemicals used for the production of integrated circuits can be quite hazardous. For example, a number of the acids are quite corrosive and/or poisonous. Therefore, the U.S. Department of Transportation (DOT) and the International Air Transportation Association (IATA) have certain requirements for the transport of such materials. One such requirement is that the material must be chemically inert and compatible with the materials of the container. This issue has already been discussed above, and has been solved with the selection of the aforementioned polyethylene and/or fluorocarbon materials. The polyethylene can be either medium density or high density, because these higher density polyethylenes are preferred for chemical resistance. Another requirement of DOT is that the sidewalls be a minimum of 0.2 mm in thickness to provide accidental rupture or leakage. Typically, plastic bottles of the prior art that are intended to be collapsible, or which are made from polystyrene, polycarbonate, or polypropylene are not chemically inert and are not approved for DOT transport. The pleated sidewall design of a preferred embodiment of the bottle of the present invention permits sidewall thickness to DOT standards, while still permitting a great deal of sidewall flexibility. Another DOT requirement is for a screw-on cap to prevent the accidental dislodgment of the cap from the neck of the bottle and to provide a leakproof fluid seal and must be certified to meet pressure testing and other requirements. Most prior art squeeze bottles are provided with "snap-on" caps which are unsuitable for the transport of hazardous liquids.

By designing the bottle of the present invention so that it can be used for sampling, storing, and transporting a chemical sample, opportunities for the contamination of the liquid sample are greatly reduced. This is because the sample is not being transferred from for example, a storage container to a transport container, with all the possibilities of contamination implicit in that transfer. Therefore, the bottle of the present invention has been designed to eliminate the need for multiple transfers of the chemical sample.

Since the bottle is used for multiple functions, a series of design decisions were made such that it is compatible with each of those functions. For example, since the sampling of a chemical sample is enhanced by allowing a substantial collapse of the bottle portion, and since the relatively inflexible medium and high density polyethylene materials are a preferred choice, the pleated sidewall design was chosen to maintain compatibility with the minimum 0.2 mm wall thickness standard of the DOT while still providing adequate flexibility to the sidewalls. As another example, since the DOT requires a threaded cap, the sampling head of the present invention was designed to be compatible with a threaded neck of a bottle portion.

In FIG. 5, sampling head 42 includes a cap portion 76 and a sampling tube portion 78. The cap portion 46 includes threads 78 which engage the threads 69 of neck 40 of bottle portion 38 (see FIG. 3a). The sampling tube 78 is an elongated, hollow tube having a length dependent upon its intended use. For example, if the sampling head 42 is to be used to obtain a chemical sample from easily accessible, open drum, the tube 78 can be 6–8 inches long. However, if the sampling head 42 is used to obtain a chemical sample from a chemical bath enclosed within a "micro environment" (i.e. a local enclosure around the chemical bath) the tube 78 can be 24 inches or longer so as to be able to reach into the bath.

The cap portion 76 and tube portion 78 of the sampling head 42 can be made from polyethylene or fluorocarbon polymers. For example, the cap portion 76 can be made from polyethylene, and the tube portion 78 can be made from PFA. As another example, both the cap portion 76 and the tube portion 78 can be made from polyethylene, either Us a one piece unit, or as a two piece unit that can be assembled. An example of a two piece unit is illustrated in FIG. 1 where a cap portion 44 is separate from the tube portion 46. FIGS. 6a–6c illustrate several preferred embodiments for the sampling head 42.

In FIG. 6a, a cap portion 76a is provided with an aperture 82 which is receptive to a tube portion 78a. In this embodiment, the cap 76a is preferably made from polyethylene, and the tube portion 78a is preferably is made from PFA. The PFA tubing can be purchased commercially, cut to size, and cleaned as will be appreciated to those skilled in the art.

In FIG. 6b, a cap portion 76b is provided with an aperture 84 receptive to a sampling tube 78b. In this embodiment, the base portion 86 of the tube 76b has been flared so that the diameter of the base portion 86 is greater than the diameter of the aperture 84. This prevents the tube 78b from being pulled from the aperture 84 of the cap portion 78b to both eliminate the inconvenience of an accidental removal of the tube from the cap, and for safely reasons. Again, the cap 76b is preferably made from polyethylene, while the tube 78b is preferably made from a length of PFA tubing.

In FIG. 6c, a sampling head 42c includes a cap portion 76c and a tube portion 78c that is formed integrally with the cap portion 76c. Since the cap portion 76c and the tube portion 76c are formed as one piece, there is little possibility of an accidental dislodgment of the tube portion 78c from the cap portion 76c. In the embodiment of FIG. 6c, both the cap portion 76c and the tube portion 78c are preferably made from polyethylene or fluoropolymers.

In FIGS. 7a and 7b, an alternate embodiment for a neck portion 88 of a bottle portion 90 is disclosed. In this embodiment, the threaded neck 88 has a solid top surface 92 formed integrally with a sampling tube 94. Liquid is drawn through the hollow interior 96 of the sampling tube 94 into the internal volume of the bottle 90. After the liquid sample has been obtained, the sampling tube 94 can "snap" off from the upper surface 92 along a score mark 98 and a solid cap, such as solid cap 22, can then be engaged with the threads 100 of the neck 88. In the embodiment of FIGS. 7a and 7b, the sampling tube 94 is made from the same material as the bottle portion 90, which is preferably polyethylene or fluoropolymers.

As noted previously, the bottle 18 is preferably provided with a solid cap 22 and a bottle portion 38. Alternatively, the bottle can be provided with a sampling head 42 (which is a form of a "cap"), rather than the solid cap 22. In this instance, the sampling head 42 will need to be sealed in some fashion (i.e. to form a "solid cap" in that instance) from the ambient environment to prevent contamination of the bottle portion 38. The cap 22 can also be provided in the kit 20 in loose form so that the bottles 18a–18d car be subsequently sealed for DOT compliant transport.

Figure 8A:
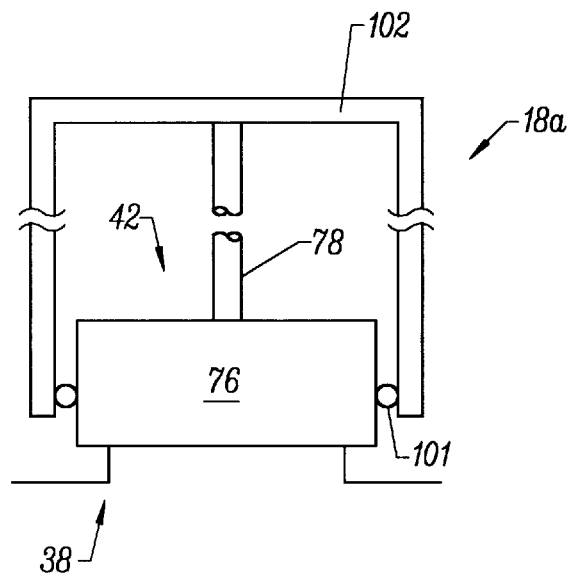
FIGS. 8a–8d illustrate several preferred methods for keeping the sampling head clean prior to use.

In FIG. 8a, a cylindrical cover 102 provided with an O-ring seal 104 is placed over the sampling tube 78 and engaged with the sidewalls of the cap portion 76. This protects the sampling tube 78 and the interior of the bottle portion 38 from the ambient environment. The cover 102 is preferably made from either polyethylene or PFA.

Figure 8B:
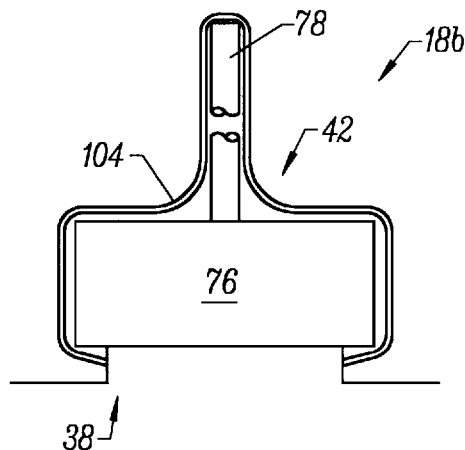

In FIG. 8b, the sampling head 42 is encased within "shrink wrap" cover 104, again to prevent contamination of the tube 78 and the interior of the bottle portion 38. The shrink wrap) material is typically made from polypropylene, and its manufacture and use are well known to those skilled in the art.

Figure 8C:
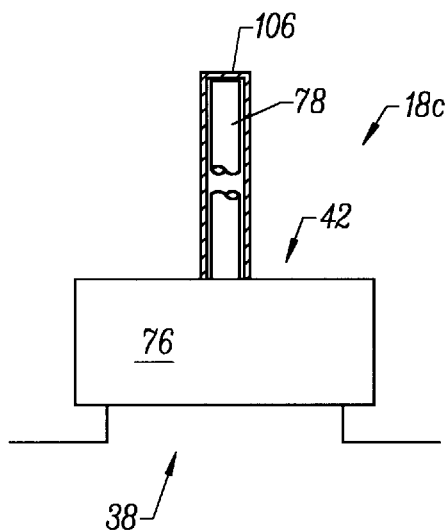

In FIG. 8c, a "friction" cover 106 is slipped over the tube 78 to perform the aforementioned protective function. The friction cover 106 is, essentially, another tube with a sealed end which frictionally engages the sidewalls of the tube 78. The friction cover can be made from any suitable material, such as polypropylene, polyethylene, etc.

Figure 8D:
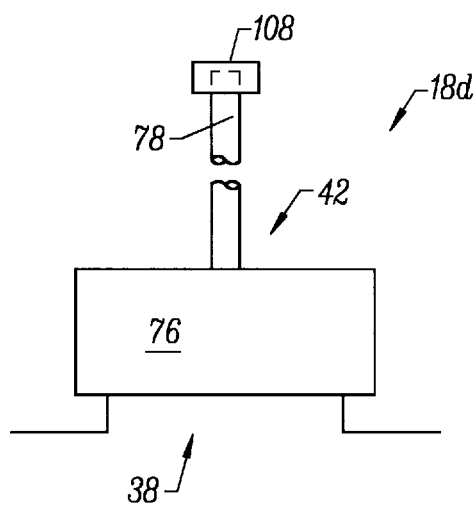

In FIG. 8d, a small cover 108 is slipped over the end of the sampling tube 78 to prevent the interior of the bottle portion 38 from being contaminated. However, it should be noted that the embodiment of FIG. 8d does not keep the entire length of the sampling tube 78 clean, as did the previously discussed embodiment of FIGS. 8a–8c. Therefore, a cleaning of the sampling tube 78 may be required prior to obtaining L sample from the bulk container of liquid. The cover 108 can be made from any of the aforementioned suitable materials.

It may be convenient to provide the bottles 8a–8a essentially "ready to go" such that only the protective covering over the sampling head needs to be removed before using the bottle to collect a specimen. However, it should be noted that the collected chemical sample cannot be shipped in the bottles illustrated in FIGS. 8a–8d by merely re-engaging the protective member. This is because, as discussed previously, the Department of Transportation (DOT) requires that plastic bottles containing hazardous liquids be shipped in containers with the screwed-on tops. Therefore, in each of the instances of FIGS. 8a–8d, the test head 42 must be removed and replaced with a cap 22 when transporting chemical samples over public roads. However, before the bottles are used, the sampling heads along with the protective members can be considered equivalent of the "solid" cap 22 in that they seal the internal volume of the bottle portion 38 from the ambient environment.

Figure 9:
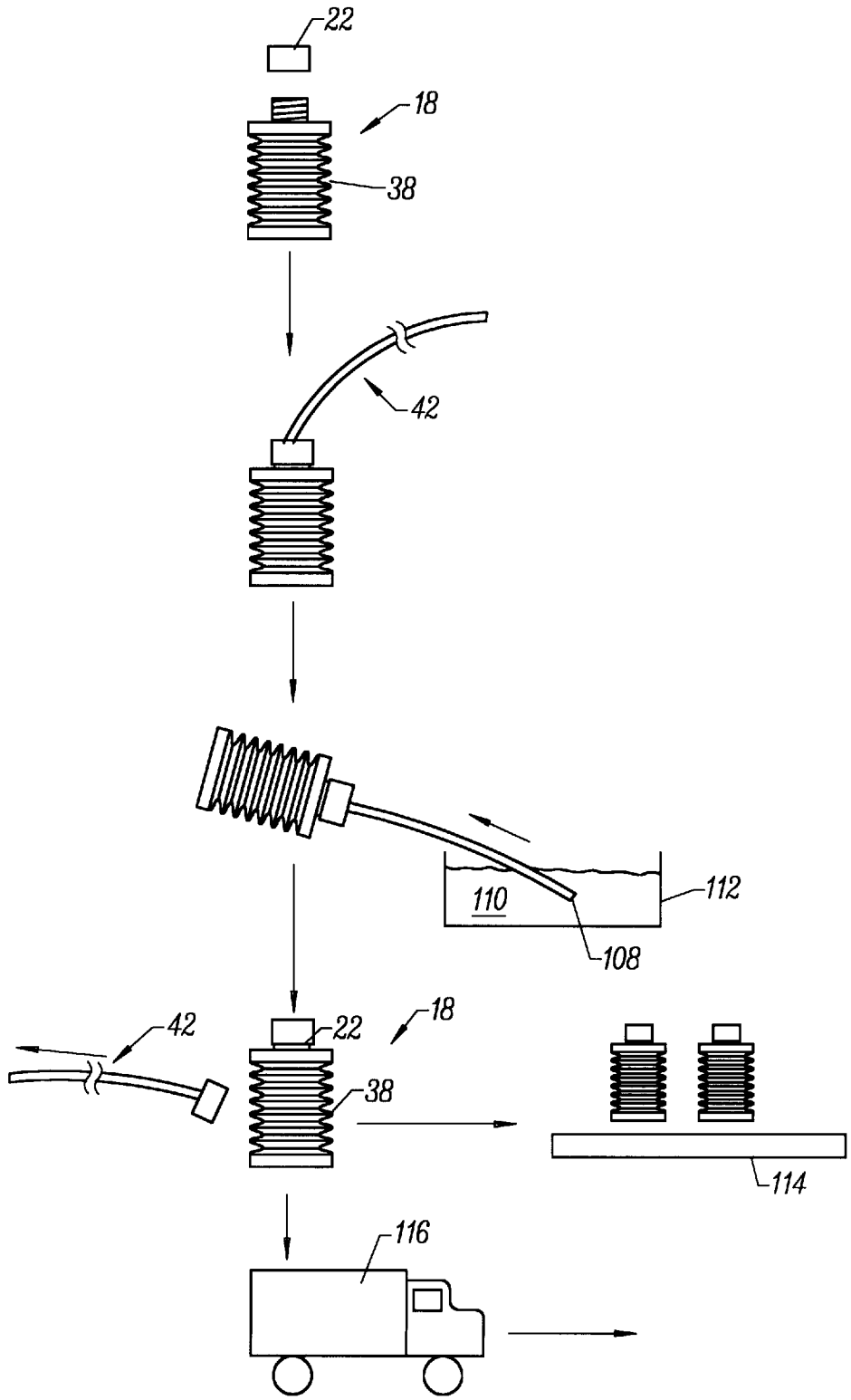
FIG. 9 is a pictorial view of the method for sampling, storing, and transporting chemical sample's in accordance with the present invention.
Figure 10:
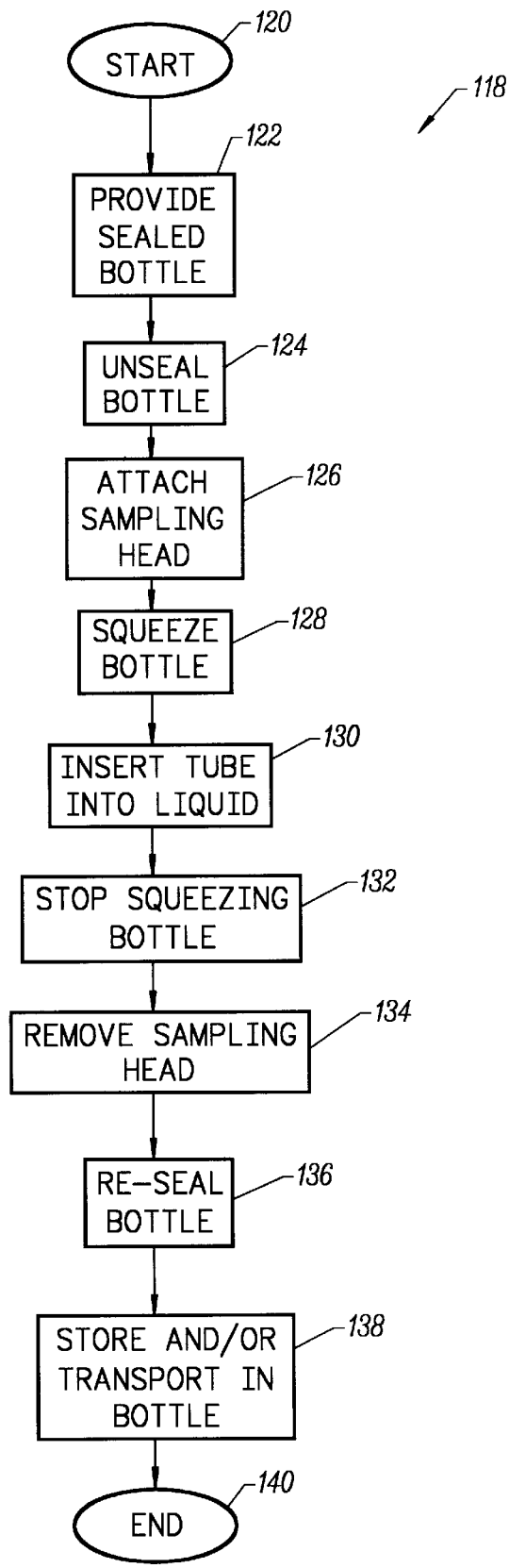
FIG. 10 is a flow diagram illustrating the method for sampling, storing, and transporting chemicals in accordance with the present invention.

The process for sampling, storing, and transporting chemical samples in accordance with the present invention will be first discussed in a pictorial fashion with reference to FIG. 9 and then as a series of process steps with reference to FIG. 10. In FIG. 9, a bottle 18 manufactured in accordance with the present invention is obtained, and the cap 22 is removed. Next, a sampling head 42 is engaged with the bottle 38, and a free end 108 is immersed into a liquid 110 which is contained within a drum, cleaning bath, holding tank, or other open container 112. The compressed bottle is released to draw liquid into the bottle portion 38 by a suction or vacuum force, after which the sampling head 42 is removed and the solid cap 22 is replaced. Preferably, the sampling head 42 is discarded in an environmentally conscious matter, such as into an acid-contamination disposal bin. The bottle 18 including the liquid sample can then be either put into archival storage 114 or it can be transported, such as within a truck 116 or other form of transportation, such as an a plane.

It should be noted from the discussion of FIG. 9, that a single bottle 18 is used to sample, store, and transport the chemical sample. This minimizes contamination problems as was discussed previously. Furthermore, the bottle 18 has been designed for multiple purposes, namely the efficient extraction of a chemical sample, the effective long-term storage of a chemical sample, and the safe transport of a chemical sample.

In FIG. 10, the process 118 for obtaining, storing, and transporting chemical samples will be discussed on a step-by-step basis. The process 118 begins at 120 and, in a step 122, a sealed bottle is provided by the manufacturing method of the present invention. Next, in a step 124, the bottle is unsealed, and the sampling head is attached in a step 126. The bottle is squeezed in a step 128, and the sampling tube is inserted into the liquid in a step 130. The bottle is then "released" (i.e. the squeezing force is removed), allowing the bottle to retain its original shape and to draw liquid into the bottle by a suction or vacuum forced caused by the release of the bottle. The amount of liquid to be drawn into the bottle will vary dependent upon the type of chemical being sampled, the number of tests to be performed, etc. However, typically about 5 ml to 100 ml of liquid is sufficient for most testing and archival purposes. It would be unusual that more than 1000 ml or less than 1 ml would be required. Next, in a step 134, the sampling head is removed, and the bottle is resealed with the solid cap in a step 136. Finally, in a step 138, the bottle is either stored, transported, or both, and the process is completed as indicated at 140.

While the bottle of the present invention is preferably disposable, it may be cleaned for re-use. For example, the bottle portion, cap, and sampling head can be soaked in nitric acid for a period of time, and then soaked in hydrochloric acid for a period of time. The acid soak treatments are then followed with rinsing and soaking in 18 megohm (M$\Omega$) water, which is changed frequently until use. However, it is intended that the bottle of the present invention can be made inexpensively enough that it can be disposed of in an environmentally safe manner after it has been used.

While this invention has been described in terms of several preferred embodiments, there are alterations, permutations, and equivalents which fall within the scope of this invention. For example, while this invention has been discussed with reference to the semiconductor manufacturing and its related industry, the processes and apparatus of the present invention are also applicable to aspects of other industries, such as the biotechnology, pharmaceutical, chemical, hard disk drive, flat panel display, and environmental industries that require an ultrapure method and apparatus for sampling clean liquids. It should also be noted that there are may alternative ways of implementing both the process and apparatus of the present invention. It is therefore intended that the following appended claims be interpreted as including all such alterations, permutations, and equivalents as fall within the true spirit and scope of the present invention.

We claim:

1. A method for sampling, storing, and transporting chemical samples comprising:

providing a sealed bottle including a bottle portion and a cap portion, said bottle portion defining an internal volume, said bottle portion having a flexible sidewall portion which permits the reduction of said internal volume in response to a pressure applied thereto, said bottle portion having a threaded neck, said bottle portion being made from a material selected from the group consisting essentially of hydrocarbon polymers and fluorocarbon polymers, said material generating less than 1 ppb of leachable metal contaminants and 1 ppm of leachable anionic and organic contaminants, said flexible sidewall portion having a minimum thickness of 0.2 mm, said a cap portion being provided with threads that are engaged with said threaded neck of said bottle portion to provide a fluid-tight seal between said internal volume of said bottle portion and the ambient environment, said cap portion being made from a material selected from the group consisting essentially hydrocarbon polymers and fluorocarbon polymers, said material generating less than 1 ppb of leachable metal contaminants and 1 ppm of leachable anionic and organic contaminants;

unsealing said sealed bottle;

attaching a sampling head including a tube to said threaded neck of said bottle portion;

exerting a force on said flexible sidewall portion to reduce said internal volume of said bottle portion;

inserting a free end of said tube into a liquid chemical to be sampled, said tube being coupled at its other end to said bottle portion, said tube being made from a material selected from the group consisting essentially of hydrocarbon polymers and fluorocarbon polymers, said tube generating less than 1 ppb of leachable metal contaminants and 1 ppm of leachable anionic and organic contaminants;

removing said force on said flexible sidewall portion to allow said internal volume of said bottle portion to increase, thereby drawing said liquid chemical through said tube to provide a chemical sample within said bottle portion; and resealing said bottle for the storage and transport of said chemical sample without transferring said chemical sample to another container.

2. A method for sampling, storing, and transporting chemical samples as recited in claim 1 wherein said hydrocarbon polymers are selected from the group consisting essentially of low density polyethylene, medium density polyethylene, and high density polyethylene, and wherein said fluorocarbon polymers are selected from the group consisting essentially of PFA, FEP, PTFE, and PEEK.

3. A method for sampling, storing, and transporting chemical samples as recited in claim 1 wherein said threaded cap portion and said bottle portion are both chemically inert and compatible with process chemicals comprising hydrofluoric acid (HF), hydrochloric acid (HCL), sulfuric acid ($H_2SO_4$), phosphoric acid ($H_3P0_4$), nitric acid ($HNO_3$), ammonium hydroxide ($H_2O_2$), ammonium hydroxide ($NH_4OH$), tetramethyl ammonium hydroxide (TMAH), and isopropyl alcohol (IPA).

4. A method for sampling, storing, and transporting chemical samples as recited in claim 3 wherein said threaded cap portion and said bottle portion are further both chemically inert and compatible with developers, strippers and photoresists used in semiconductor manufacturing processes.

5. A method for sampling, storing, and transporting chemical samples as recited in claim 1 wherein said hydrocarbon polymers include one or more of low density polyethylene, medium density polyethylene, and high density polyethylene, and wherein said fluorocarbon polymers include one or more of PFA, FEP, PTFE, and PEEK.

6. A method for sampling, storing, and transporting chemical samples as recited in claim 1 further comprising, after removing said force, unattaching said sampling head from said threaded neck of said bottle.

7. A method for sampling, storing, and transporting chemical samples as recited in claim 1 wherein said threaded cap portion and said bottle portion are both chemically inert and compatible with a number of acids, bases, solvents, developers, strippers and photoresists used in semiconductor manufacturing processes.

8. A method for sampling, storing, and transporting chemical samples as recited in claim 1 wherein said flexible sidewall portion is pleated.

9. A method for sampling, storing, and transporting chemical samples as recited in claim 8 wherein said flexible sidewall portion is pleated concentrically with a vertical axis of said bottle portion.

10. A method for sampling, storing, and transporting chemical samples as recited in claim 1 wherein said flexible sidewall portion is generally cylindrical.

11. A method for sampling, storing, and transporting chemical samples as recited in claim 1 wherein said cap portion is a solid cap which provides a fluid-tight seal between said internal volume of said bottle portion and the ambient environment.

12. A method for sampling, storing, and transporting chemical samples as recited in claim 1 wherein said sampling head includes a sampling head cap provided with an aperture, wherein said tube extends through said aperture of said sampling head cap.

13. A method for sampling, storing, and transporting chemical samples as recited in claim 12 wherein said tube is provided with a flared end to inhibit the removal of said tube from said aperture.

14. A method for sampling, storing, and transporting chemical samples as recited in claim 1 wherein said sampling head includes a sampling head cap provided with an aperture, wherein said tube is integral with said sampling head cap and in fluid communication with said aperture.

15. A method for sampling, storing, and transporting chemical samples comprising:

providing a sealed bottle including a bottle portion and a cap portion, said bottle portion defining an internal volume, said bottle portion having a flexible sidewall portion which permits the reduction of said internal volume in response to a pressure applied thereto, said bottle portion having a neck, said bottle portion being made from a material selected from the group consisting essentially of hydrocarbon polymers and fluorocarbon polymers, said material generating less than 1 ppb of leachable metal contaminants and 1 ppm of leachable anionic and organic contaminants, said flexible side, all portion having a minimum thickness, said cap portion being made from a material selected from the group consisting essentially hydrocarbon polymers and fluorocarbon polymers, said material generating less than 1 ppb of leachable metal contaminants and 1 ppm of leachable anionic and organic contaminants;

unsealing said sealed bottle;

attaching a sampling head including a tube to said neck of said bottle portion;

exerting a force on said flexible sidewall portion to reduce said internal volume of said bottle portion;

inserting a free end of said tube into a liquid chemical to be sampled, said tube being coupled at its other end to said bottle portion, said tube being made from a material selected from the group consisting essentially of hydrocarbon polymers and fluorocarbon polymers, said tube generating less than 1 ppb of leachable metal contaminants and 1 ppm of leachable anionic and organic contaminants;

removing said force on said flexible sidewall portion to allow said internal volume of said bottle portion to increase, thereby drawing said liquid chemical through said tube to provide a chemical sample within said bottle portion; and resealing said bottle for the storage and transport of said chemical sample without transferring said chemical sample to another container.

16. A method for sampling, storing, and transporting chemical samples as recited in claim 15 wherein said hydrocarbon polymers are selected from the group consisting essentially of low density polyethylene, medium density polyethylene, and high density polyethylene, and wherein said fluorocarbon polymers are selected from the group consisting essentially of PFA, ITP, PFEE, and PEEK.

17. A method for sampling, storing, and transporting chemical samples as recited in claim 15 wherein said cap portion and said bottle portion are both chemically inert and compatible with at least one acid, base, solvent, developer, stripper or photoresist used in a semiconductor manufacturing process.

18. A method for sampling, storing, and transporting chemical samples as recited in claim 15 wherein said flexible sidewall portion is pleated.

19. A method for sampling, storing, and transporting chemical samples as recited in claim 15 wherein said flexible sidewall portion is substantially cylindrical.

20. A method for sampling, storing, and transporting chemical samples comprising:

providing a sealed bottle including a bottle portion having a cap attachment region and a cap portion engageable with said cap attachment region, said bottle portion defining an internal volume, said bottle portion having a flexible sidewall portion which permits the reduction of said internal volume in response to a pressure applied thereto, said bottle portion being made from a material selected from the group consisting essentially of hydrocarbon polymers and fluorocarbon polymers, said material generating less than 1 ppb of leachable metal contaminants and 1 ppm of leachable anionic and organic contaminants, said cap portion being made from a material selected from the group consisting essentially hydrocarbon polymers and fluorocarbon polymers, said material generating less than 1 ppb of leachable metal contaminants and 1 ppm of leachable anionic and organic contaminants;

unsealing said sealed bottle;

attaching a sampling head including a tube to said cap attachment region of said bottle portion;

exerting a force on said flexible sidewall portion to reduce said internal volume of said bottle portion;

inserting a free end of said tube into a liquid chemical to be sampled, said tube being coupled at its other end to said bottle portion, said tube being made from a material selected from the group consisting essentially of hydrocarbon polymers and fluorocarbon polymers, said tube generating less than 1 ppb of leachable metal contaminants and 1 ppm of leachable anionic and organic contaminants;

removing said force on said flexible sidewall portion to allow said internal volume of said bottle portion to increase, thereby drawing said liquid chemical through said tube to provide a chemical sample within said bottle portion; and resealing said bottle for the storage and transport of said chemical sample without transferring said chemical sample to another container.

* * * * *

UNITED STATES PATENT AND TRADEMARK OFFICE
CERTIFICATE OF CORRECTION

PATENT NO. : 5,804,744
DATED : September 8, 1998
INVENTOR(S) : Tan et al.

It is certified that error appears in the above-indentified patent and that said Letters Patent is hereby corrected as shown below:

Column 1, line 25, change "he" to --the--
Column 4, line 22, change "HFA" to --PFA--
Column 4, line 62, change "to" to --do--
Column 5, line 39, change "blot" to --blow--
Column 6, line 62, change "pre-c leaning" to --pre-cleaning--
Column 7, line 42, change "sample's" to --samples--
Column 9, line 7, change "blot" to --blow--
Column 9, line 57, change "anti/or" to --and/or--
Column 12, line 32, change "p)resent" to --present--
Column 14, line 46, change "car" to --can--
Column 15, line 6, change "L" to --a--
Column 15, line 44, change "a plane" to --airplane--
Column 16, line 29, change "may" to --many--

Column 18, line 28, change "side,all" to --sidewall--
Column 18, line 61, change "ITP, PFEE" to --FEP, PTFE--

Signed and Sealed this

Twelfth Day of October, 1999

Attest:

Q. TODD DICKINSON

*Attesting Officer*          *Acting Commissioner of Patents and Trademarks*